US010067070B2

United States Patent
Tedeschi et al.

(10) Patent No.: US 10,067,070 B2
(45) Date of Patent: Sep. 4, 2018

(54) PARTICLE MONITORING DEVICE

(71) Applicant: Applied Materials, Inc., Santa Clara, CA (US)

(72) Inventors: Leonard Tedeschi, San Jose, CA (US); Kartik Ramaswamy, San Jose, CA (US)

(73) Assignee: Applied Materials, Inc., Santa Clara, CA (US)

( * ) Notice: Subject to any disclaimer, the term of this patent is extended or adjusted under 35 U.S.C. 154(b) by 11 days.

(21) Appl. No.: 14/935,186

(22) Filed: Nov. 6, 2015

(65) Prior Publication Data

US 2017/0131217 A1    May 11, 2017

(51) Int. Cl.
*G01N 21/00* (2006.01)
*G01N 21/94* (2006.01)
*G01N 21/95* (2006.01)
*H01L 21/66* (2006.01)

(52) U.S. Cl.
CPC ......... *G01N 21/94* (2013.01); *G01N 21/9501* (2013.01); *H01L 22/20* (2013.01)

(58) Field of Classification Search
CPC .......... G01N 21/9501; G01N 23/2251; G01N 23/20; G01N 21/94; G01N 23/225; G01N 21/47; G01N 21/8851; G01N 21/956; G01N 2021/8967; G01N 2033/0095; H01L 22/12
USPC .......................................... 356/237.1–237.7
See application file for complete search history.

(56) References Cited

U.S. PATENT DOCUMENTS

| | | | |
|---|---|---|---|
| 5,943,130 A * | 8/1999 | Bonin .............. | G01N 15/0205 356/237.5 |
| 6,696,362 B2 | 2/2004 | Rossman et al. | |
| 7,166,480 B2 | 1/2007 | Shiraishi et al. | |
| 7,521,915 B2 | 4/2009 | Herchen et al. | |
| 7,567,072 B2 | 7/2009 | Orvek et al. | |
| 8,823,933 B2 | 9/2014 | Bonciolini et al. | |
| 2003/0115978 A1 | 6/2003 | Moehnke et al. | |
| 2005/0093612 A1* | 5/2005 | Gilliam .............. | G01R 31/3004 327/534 |
| 2008/0228419 A1 | 9/2008 | Renken | |
| 2008/0239314 A1 | 10/2008 | Bonciolini et al. | |
| 2008/0258057 A1 | 10/2008 | Williamson et al. | |

(Continued)

OTHER PUBLICATIONS

PCT International Search Report and Written Opinion for PCT International Appln No. PCT/US2016/056846 dated Jan. 20, 2017. (13 pages).

(Continued)

*Primary Examiner* — Sunghee Y Gray
(74) *Attorney, Agent, or Firm* — Schwabe, Williamson & Wyatt, P.C.

(57) ABSTRACT

Embodiments include devices and methods for detecting particles in a wafer processing tool. In an embodiment, a particle monitoring device having a wafer form factor includes several micro sensors capable of operating in all pressure regimes, e.g., under vacuum conditions. The particle monitoring device may include a clock to output a time value when a parameter of a micro sensor changes in response to receiving a particle within a chamber of the wafer processing tool. A location of the micro sensor or the time value may be used to determine a source of the particle. Other embodiments are also described and claimed.

14 Claims, 7 Drawing Sheets

(56) References Cited

U.S. PATENT DOCUMENTS

2009/0296273 A1* 12/2009 Kurashima ........ G11B 33/1446
360/97.12
2011/0315985 A1 12/2011 Oba et al.
2016/0198129 A1* 7/2016 Proud ................... A61B 5/1118
348/143

OTHER PUBLICATIONS

Harash Ajjam, "Individual Air-Borne Particle Mass Measurement Using High-Frequency Micromechanical Resonators", IEEE Sensors Journal, vol. 11, No. 11, Nov. 2011, pp. 2883-2890.
International Preliminary Report on Patentability from PCT/US2016/056846 dated May 8, 2018, 8 pgs.

* cited by examiner

PARTICLE MONITORING DEVICE

BACKGROUND

1) Field

Embodiments relate to the field of semiconductor processing and, in particular, to devices and methods for detecting particles in a wafer processing tool.

2) Description of Related Art

A primary concern in the manufacture of semiconductor devices is particle contamination of a semiconductor wafer. Such contamination typically occurs during one or more operations performed by a wafer processing tool during manufacture of the semiconductor devices. For example, the wafer processing tool includes several interfaces, e.g., several chambers interconnected by load locks, and the actuation or operation of any of these system components may generate metallic or nonmetallic particles such as aluminum, stainless steel, zirconium, or other particles that can contaminate a semiconductor wafer in the tool.

To identify a source and/or root cause of particle contamination, semiconductor wafers are periodically processed through one or more chambers of the wafer processing tool and then subjected to a particle inspection operation. The particle inspection operation requires the processed wafer to be queued for inspection by optical inspection equipment to identify a location and general size of particles, and then queued for inspection by scanning electron microscopy, energy dispersive spectroscopy, or other inspection techniques to determine a presence and/or composition of particles on the wafer. After detecting the presence and composition of the particles, additional troubleshooting may be required to identify which of the operations performed by the wafer processing tool actually led to the particle contamination.

SUMMARY

Embodiments include a particle monitoring device to detect particles within a wafer processing tool. In an embodiment, the particle monitoring device includes a substrate having a support surface, and a micro sensor mounted at a predetermined location on the support surface. The micro sensor may have a parameter, and the parameter may change when the micro sensor receives a particle within a chamber of the wafer processing tool. A clock and a processor may also be mounted on the substrate. The clock may be configured to output a time value. Furthermore, the processor may be operably connected to the micro sensor and the clock, and the processor may be configured to record the predetermined location of the micro sensor and the time value output by the clock when the parameter of the micro sensor changes, e.g., when the particle contacts the micro sensor.

The particle monitoring device may include additional components. For example, a memory may be mounted on the substrate, and the processor may be operably connected to the memory to record the predetermined location and the time value in the memory. Similarly, a power source may be mounted on the substrate, and the power source may be electrically connected to one or more of the other components, such as the micro sensor, the clock, the processor, or the memory, to power the components.

The particle monitoring device may be configured to be moved between chambers of the wafer processing tool. For example, the substrate of the particle monitoring device may include a semiconductor material having a wafer form factor. In an embodiment, the wafer form factor includes a diameter between 95 to 455 mm, e.g., 300 mm.

The particle monitoring device may include numerous micro sensors distributed across the support surface of the substrate, and each micro sensor may be of a respective sensor type. In an embodiment, the micro sensors include a MOSFET and a collector. The parameter of the micro sensor may be a threshold voltage of the MOSFET. Furthermore, the collector may be electrically coupled to the MOSFET such that the threshold voltage changes in response to a particle contacting the collector.

The micro sensor may detect particle behavior other than contact between the particle and the sensor. For example, the micro sensor may include an optical sensor having an optical path. In an embodiment, the parameter of the micro sensor changes in response to a particle disturbing the optical path.

In an embodiment, a micro-resonator may be mounted on the support surface of the particle monitoring device. The micro-resonator may have a characteristic frequency, and the characteristic frequency may shift when the micro-resonator receives a particle within a chamber of the wafer processing tool. The characteristic frequency may be inversely proportional to a mass of the micro-resonator. Thus, when the micro-resonator receives the particle, e.g., when the particle lands on the macro resonator, the mass and the characteristic frequency of the micro-resonator changes. The processor may be configured to record the predetermined location of the micro-resonator and the time value output by the clock when the characteristic frequency shifts.

A particle monitoring device having a micro-resonator may include additional components to facilitate the micro-resonator function. For example, a broad frequency source may be mounted on the substrate to excite the micro-resonator. Furthermore, a detector may be mounted on the substrate to detect the shift of the characteristic frequency. Thus, the electronic circuitry of the particle monitoring device may be adapted to the type of micro sensors distributed across the substrate.

An embodiment also includes a method for determining a source of a particle in a wafer processing tool. In an embodiment, the method includes moving a particle monitoring device from a first chamber to a second chamber of the wafer processing tool. The particle monitoring device may include a structure as described above. For example, the particle monitoring device may have a micro sensor mounted at a predetermined location on a support surface of a substrate, and a clock mounted on the substrate. The micro sensor may have a parameter, and the clock may be configured to output a time value. The method may include detecting a change of the parameter when the micro sensor receives a particle within the second chamber. Detecting the change of the parameter may include detecting a change in a parameter of a MOSFET, an optical sensor, or a micro-resonator, as described above. In an embodiment, a chamber pressure of the second chamber is reduced to a vacuum condition before the micro sensor receives the particle within the second chamber. Thus, the method for determining the source of the particle using the particle monitoring device may be carried out in all pressure regimes. The method may also include recording the predetermined location of the micro sensor and the time value output by the clock in response to detecting the change of the parameter. A source of the particle may then be determined based on one or more of the recorded predetermined location or the recorded time value.

The above summary does not include an exhaustive list of all aspects. It is contemplated that all systems and methods are included that can be practiced from all suitable combinations of the various aspects summarized above, as well as those disclosed in the Detailed Description below and particularly pointed out in the claims filed with the application. Such combinations have particular advantages not specifically recited in the above summary.

DETAILED DESCRIPTION

Figure 2:
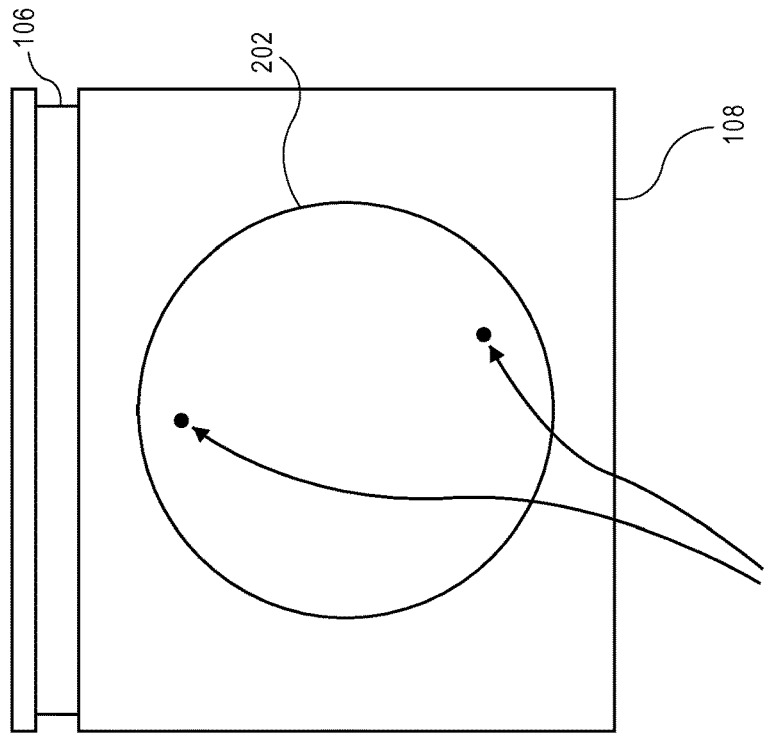
FIG. 2 is a sectional illustration of a semiconductor wafer in a chamber of a wafer processing tool, in accordance with an embodiment.

Devices and methods used for detecting particles in a wafer processing tool are described in accordance with various embodiments. In the following description, numerous specific details are set forth in order to provide a thorough understanding of embodiments. It will be apparent to one skilled in the art that embodiments may be practiced without these specific details. In other instances, well-known aspects are not described in detail in order to not unnecessarily obscure embodiments. Furthermore, it is to be understood that the various embodiments shown in the accompanying drawings are illustrative representations and are not necessarily drawn to scale.

Existing techniques for identifying the presence, composition, or source of particle contamination in a semiconductor wafer are time-consuming, expensive, and difficult. Distances between a wafer processing tool and defect inspection equipment, as well as work queues for the inspection equipment, can mean that the inspection process takes an hour or more, delaying mean time to repair the wafer processing tool. The inspection equipment is also expensive, costing in the range of several million dollars to buy, and requiring fabrication facility space for non-value-added wafer inspection equipment. Furthermore, the troubleshooting process used to identify the exact operation that caused the particle contamination is tedious to perform, and uses numerous wafers costing more than a hundred dollars each.

In an aspect, a particle monitoring device allows for system-level particle detection in a wafer processing tool at all pressure regimes. The particle monitoring device may include numerous micro sensors built into a wafer form factor such that the particle monitoring device can be moved between chambers of the wafer processing tool and can be subjected to the same process operations as would be a semiconductor wafer. Thus, the particle monitoring device may collect real-time information about the precise time when (and the precise location where) a particle lands on the wafer-like device during the wafer fabrication process, including during process operations performed under vacuum conditions. Accordingly, a source and root cause of particle contamination may be determined quickly and without the need for expensive inspection equipment or tedious troubleshooting. This can reduce mean time to repair the wafer processing tool, or can reduce time to qualify the wafer processing tool for production. Furthermore, the particle monitoring device can replace costly defection inspection equipment and free up fabrication facility space for value added wafer processing equipment.

It will be understood that the particle monitoring devices and methods described below could be used in any form factor or process where particles are yield limiting. More particularly, although the particle monitoring devices and methods are described with respect to wafer processing for the fabrication of integrated circuits, the devices and methods may also be adapted for use in other technologies, such as displays in the electronics industry and/or photovoltaic cells in the solar industry. Similarly, the devices and methods may be applicable to determining process uniformity, in addition to or instead of detecting particles. For example, a particle monitoring device as described below may be adapted to determine plasma, deposition, or illumination uniformity during a wafer fabrication process.

Figure 1:
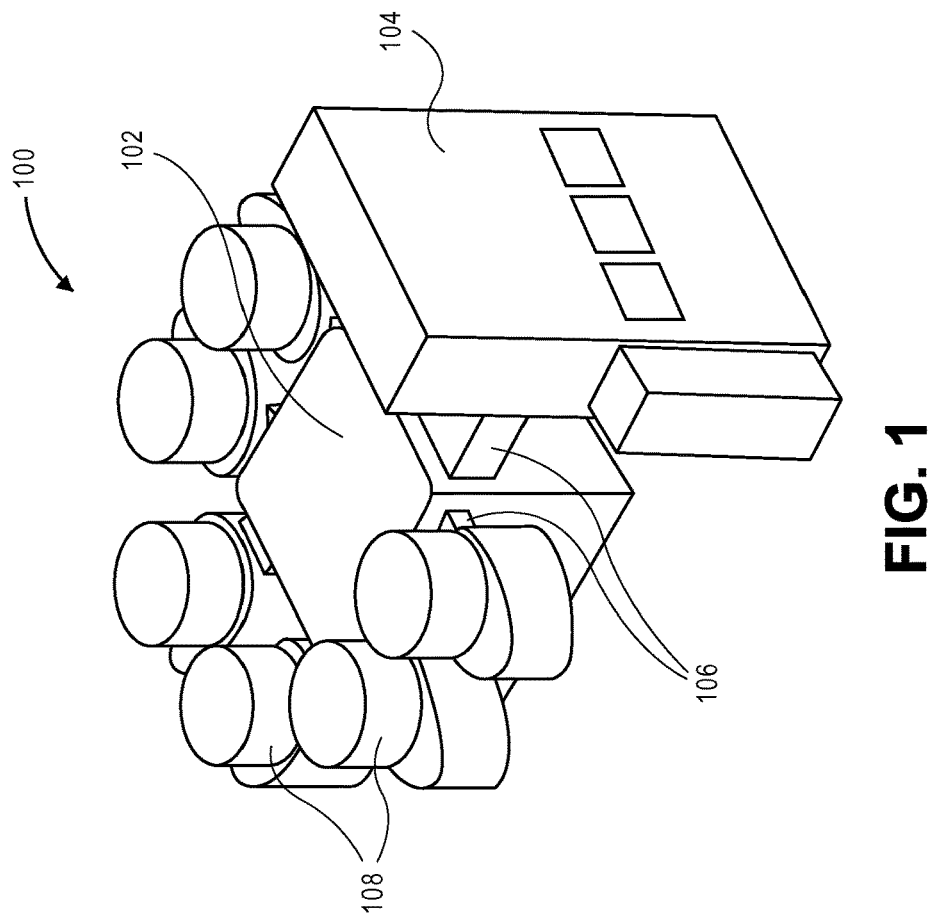
FIG. 1 is an illustration of a wafer processing tool, in accordance with an embodiment.

Referring now to FIG. 1, an illustration of a wafer processing tool is illustrated in accordance with an embodiment. A wafer processing tool 100 may include a buffer chamber 102 physically connected to a factory interface 104 by one or more load locks 106. Furthermore, one or more processing chambers 108 may be physically connected to buffer chamber 102 by one or more respective load locks 106. Buffer chamber 102 may essentially act as an intermediate volume, larger than respective volumes of processing chambers 108, that remains at a low pressure, albeit at a pressure higher than the process pressures within processing chambers 108. Thus, a semiconductor wafer, e.g., a silicon wafer, may be moved between chambers of wafer processing tool 100 under vacuum conditions during the manufacture of semiconductor devices. This movement may be enabled by various devices included in the wafer processing tool 100, e.g., robotic arms, shuttles, etc.

Various manufacturing operations may be performed in processing chambers 108. For example, at least one of processing chambers 108 may be a plasma etch chamber, a deposition chamber, a chamber of a semiconductor lithography tool, or any other semiconductor process tool chamber. As such, processing chamber 108 may be used to perform manufacturing processes under vacuum conditions, atmospheric conditions, or any other pressure regime.

A semiconductor wafer may be subjected to different pressure conditions as the wafer moves through the wafer processing tool 100. For example, the semiconductor wafer may be inserted into the factory interface 104 at atmospheric conditions. Then, as the semiconductor wafer goes into a load lock 106 between factory interface 104 and buffer chamber 102, the load lock 106 may be brought to a vacuum condition of 120 millitorr. The semiconductor wafer may then pass from the load lock 106 into buffer chamber 102, having a buffer chamber pressure of 100 millitorr.

Referring now to FIG. 2, a sectional illustration of a semiconductor wafer in a chamber of a wafer processing tool is illustrated in accordance with an embodiment. A semiconductor wafer 202 may be transferred from buffer chamber 102 into one of the processing chambers 108 through load lock 106. Processing chambers 108 may have a chamber pressure that is lowered, e.g., using a vacuum pump and/or turbo pump, to a vacuum condition. In the context of this description, a vacuum condition may be any pressure less than 0.5 atm. In an embodiment, the vacuum condition in processing chamber 108 exists when processing chamber 108 has a chamber pressure less than the pressure of buffer chamber 102, e.g., less than 100 millitorr. Accordingly, the manufacturing operation performed in processing chamber 108 may be carried out under vacuum conditions.

One or more particles 204 may be generated during the manufacturing operation performed in processing chamber 108. For example, particle 204 may be a metallic or non-metallic particle that is emitted into processing chamber 108 when a specific operation occurs, e.g., when a valve of the load lock 106 is opened, when a load lock door is locked, when lift pins are moving, or when any other tool operation occurs. The emitted particles 204 may land on semiconductor wafer 202, and a landing location and time of particle 204 may correspond to a source of the particle contamination. For example, particle 204 shown near an upper edge of semiconductor wafer 202 in FIG. 2 may land on semiconductor wafer 202 nearer to load lock 106 and at a time when load lock 106 is closed, indicating that a component of load lock 106 and/or the actuation of load lock 106 is the source of particle 204. Thus, it can be seen that particle monitoring that provides information about a location and a time when particle 204 lands on semiconductor wafer 202 may be useful in determining a source of particle contamination.

Figure 3:
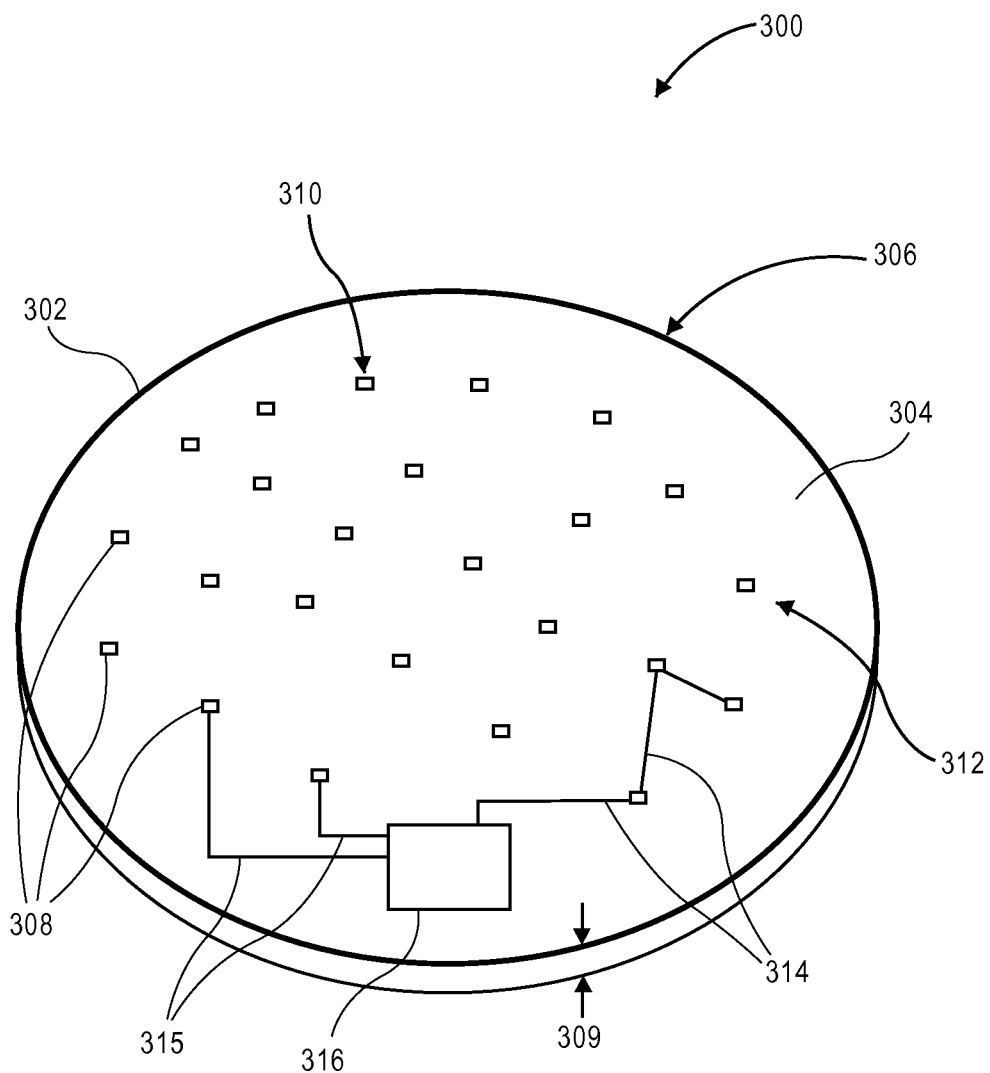
FIG. 3 is an illustration of a particle monitoring device, in accordance with an embodiment.

Referring now to FIG. 3, an illustration of a particle monitoring device is illustrated in accordance with an embodiment. Particle monitoring device 300 may be configured to be moved between chambers, e.g., buffer chamber 102 and/or processing chambers 108, of wafer processing tool 100. For example, particle monitoring device 300 may include a substrate 302 having an overall form factor and/or a same material and shape as semiconductor wafer 202. That is, substrate 302 may be at least partially composed of a semiconductor material, e.g., a crystalline silicon material. Furthermore, substrate 302 may have a wafer form factor that is essentially disc-shaped and includes a support surface 304 having a diameter 306. Support surface 304 may be an upper surface of the disc, and a bottom surface of substrate 302 (not shown) may be spaced apart from support surface 304 by a thickness 309. In an embodiment, the wafer form factor of substrate 302 includes diameter 306 between 95 to 455 mm, e.g., diameter 306 may nominally be 100 mm, 300 mm, or 450 mm. Furthermore, the wafer form factor of substrate 302 may include thickness 309 less than 1 mm, e.g., 525 µm, 775 µm, or 925 µm. Thickness 309 may also be greater than 1 mm, e.g., several millimeters up to 10 mm. Accordingly, particle monitoring device 300 may be manufactured using readily available wafer materials and typical wafer manufacturing processes and equipment, and may essentially simulate semiconductor wafer 202 when processed by wafer processing tool 100.

Particle monitoring device 300 may include several micro sensors 308 mounted on support surface 304 at predetermined locations. For example, numerous micro sensors 308, e.g., thousands to millions of micro sensors 308, may be built on support surface 304. Each micro sensor 308 may have a known location. For example, a first micro sensor may be located at a first location 310, and a second micro sensor may be located at a second location 312. Second location 312 may have a known position relative to first location 310, or relative to some other reference point on particle monitoring device 300.

Micro sensors 308 may be distributed across support surface 304 randomly or arranged in a predetermined pattern. For example, micro sensors 308 shown in FIG. 3 appear to be randomly distributed across support surface 304, even though their absolute or relative locations may be predetermined and known. In an embodiment, micro sensors 308 are arranged in a predetermined pattern, e.g., a grid pattern, a concentric circle pattern, a spiral pattern, etc. Such patterns may be achieved using known etching processes to build micro sensors 308 at precise locations on support surface 304 of particle monitoring device 300.

In an embodiment, micro sensors 308 are spread over a majority of a surface area of support surface 304. For example, an outer profile drawn through the outermost micro sensors 308 of the micro sensor array may delineate an array area that is at least half of the surface area of support surface 304. In an embodiment, the array area is at least 75% of the surface area, e.g., greater than 90% of the surface area of support surface 304.

The micro sensors 308 of particle monitoring device 300 may be interconnected with each other or other circuitry through one or more electrical connector. For example, micro sensors 308 may be connected in series by an electrical trace 314 running over support surface 304. Alternatively or in addition, several micro sensors 308 may be electrically connected in parallel by respective electrical traces 315. Thus, electrical connections may be made between micro sensors 308 and/or micro sensors 308 may be connected to electronic circuitry 316, using electrical traces, electrical leads, vias, and other known types of electrical connectors.

Each micro sensor 308 of particle monitoring device 300 may be configured to sense a change in a given parameter when particle 204 interacts with the sensor. More particularly, a micro sensor 308 may have a parameter, and the parameter may change when the micro sensor 308 receives particle 204 within a chamber, e.g., processing chamber 108, of wafer processing tool 100. Here, the term "receives" indicates an interaction between particle 204 and micro sensor 308 that affects the given parameter. For example, the parameter may be a voltage, a current, or another physical or electrical characteristic of micro sensor 308 that changes when particle 204 lands on micro sensor 308, passes near or through micro sensor 308, or impacts micro sensor 308, as described below. Other particle-sensor interactions will be understood by a skilled artisan when reading this description.

Figure 4:
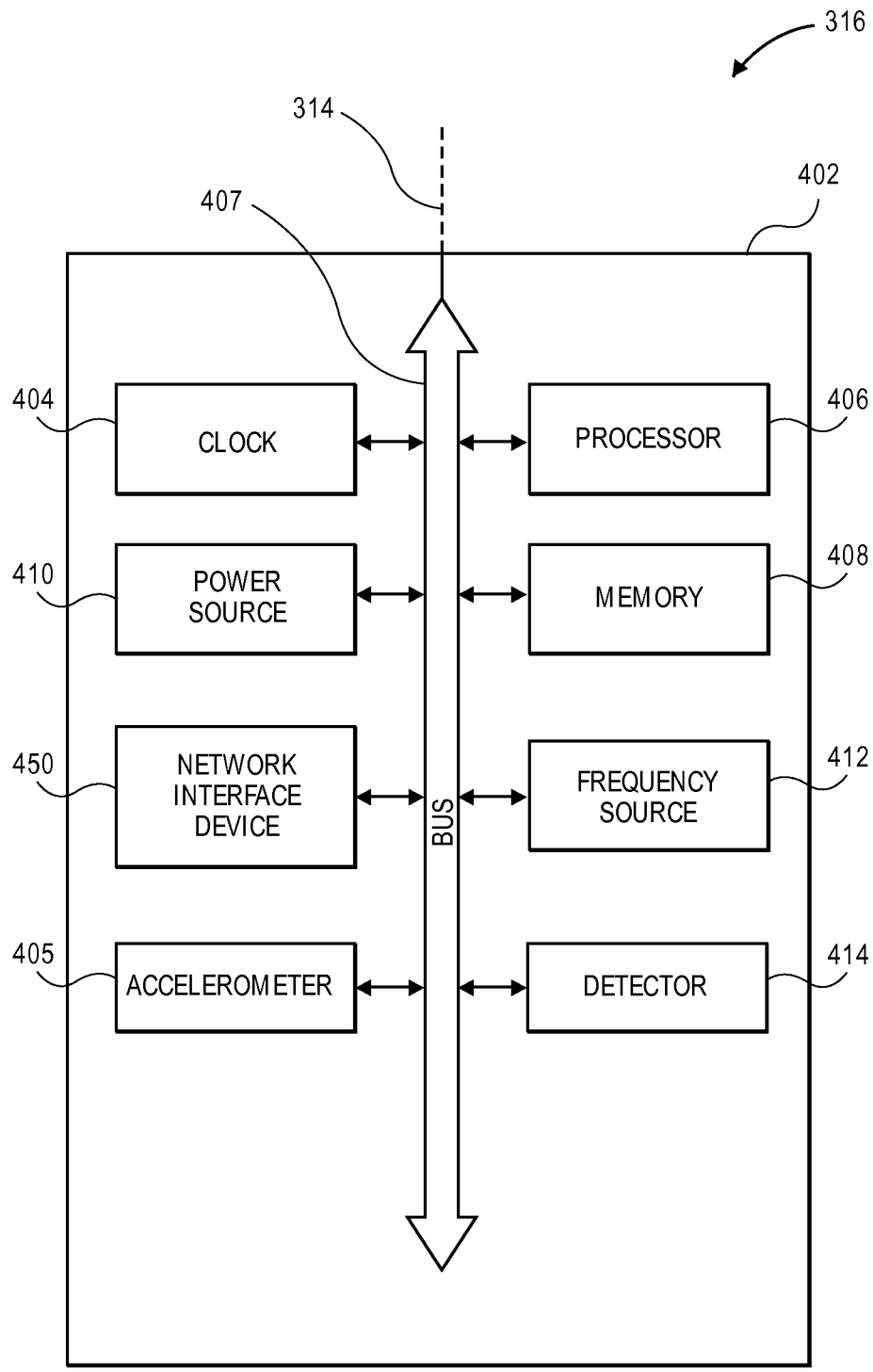
FIG. 4 is an illustration of a block diagram of electronic circuitry of a particle monitoring device, in accordance with an embodiment.

Referring now to FIG. 4, an illustration of a block diagram of electronic circuitry of a particle monitoring device is illustrated in accordance with an embodiment. Electronic circuitry 316 of particle monitoring device 300 may be enclosed or supported in a housing 402, or may be exposed to processing chamber 108. Housing 402 and/or electronic components of electronic circuitry 316 may be mounted on support surface 304 of substrate 302. In an embodiment, one or more component of electronic circuitry 316 is mounted on the bottom surface (not shown) of substrate 302, opposite from support surface 304. Electronic circuitry 316 may nonetheless be placed in electrical connection with micro sensors 308 through one or more electrical trace, electrical lead, or via, even when mounted on opposite sides of substrate 302.

Electronic circuitry 316 of particle monitoring device 300 may include a clock 404 mounted on substrate 302. Clock may be an electronic circuit having an electronic oscillator, e.g., a quartz crystal, to output an electrical signal having a precise frequency, as is known in the art. Thus, clock 404 may be configured to output a time value corresponding to the electrical signal. The time value may be an absolute time value independent of other operations, or the time value may be synchronized to other clocks in wafer processing tool 100. For example, clock 404 may be synchronized to a system clock 404 of wafer processing tool 100 such that the time value output by clock 404 corresponds to a system time value and/or system operations that are output or controlled by the system clock. Clock 404 may be configured to initiate the output of the time value when a particular process operation occurs. For example, electronic circuitry 316 may include an accelerometer 405 that triggers clock 404 to begin outputting the time value when particle monitoring device 300 leaves factory interface 104. Thus, the time value may provide information about when particle monitoring device 300 enters or exits a particular chamber or load lock of wafer processing tool 100.

Electronic circuitry 316 of particle monitoring device 300 may include a processor 406 mounted on substrate 302. Processor 406 may be operably coupled, e.g., electrically connected by bus 407 and/or traces 314, to one or more micro sensors 308 and to clock 404. Processor 406 represents one or more general-purpose processing devices such as a microprocessor, central processing unit, or the like. More particularly, processor 406 may be a complex instruction set computing (CISC) microprocessor, reduced instruction set computing (RISC) microprocessor, very long instruction word (VLIW) microprocessor, a processor implementing other instruction sets, or processors implementing a combination of instruction sets. Processor 406 may also be one or more special-purpose processing devices such as an application specific integrated circuit (ASIC), a field programmable gate array (FPGA), a digital signal processor (DSP), network processor, or the like.

Processor 406 is configured to execute processing logic for performing the operations described herein. For example, processor 406 may be configured to record the predetermined location of a micro sensor 308 and the time value output by clock 404 when the respective parameter of the micro sensor 308 changes. Accordingly, processor 406 may be configured to monitor and record a precise time when (and location where) particle 204 contacts particle monitoring device 300. Processor 406 may be configured to determine other types of information based on signals received from micro sensors 308. For example, in addition to knowing when and where particle contacted particle monitoring device 300, processor 406 may be configured to analyze a signal received from the triggered micro sensor 308 to determine a size of particle 204, a total number of particles 204 on particle monitoring device 300, a type of a particle 204 (metallic or non-metallic), etc.

Monitoring of micro sensors 308 may be performed by processor 406 on an individual or group basis. That is, processor 406 may monitor and record individual data for each micro sensor 308. Accordingly, each micro sensor 308 may be individually identifiable, e.g., by a unique sensor identification number that is associated with location or other sensor-specific data. In an embodiment, sensors may be monitored in groups. For example, processor 406 may monitor and record bank data for a group of one or more micro sensors 308. Accordingly, the group of micro sensors 308 may be associated with location or other group-specific data that corresponds to the group of sensors as a whole.

Electronic circuitry 316 of particle monitoring device 300 may include a memory 408 mounted on substrate 302. Memory 408 may include one or more of a main memory (e.g., read-only memory (ROM), flash memory, dynamic random access memory (DRAM) such as synchronous DRAM (SDRAM) or Rambus DRAM (RDRAM), etc.), a static memory (e.g., flash memory, static random access memory (SRAM), etc.), or a secondary memory (e.g., a data storage device). Processor 406 may communicate with memory 408 via bus 407 or other electrical connection. Thus, processor 406 may be operably coupled to memory 408 to record the predetermined location of the triggered micro sensor 308 and the time value output by clock 404, in the memory 408. That is, memory 408 may log when micro sensor 308 interacts with particle 204. More particularly, memory 408 can log a time when, and a location where, micro sensor 308 receives particle 204.

Electronic circuitry 316 of particle monitoring device 300 may include a power source 410 mounted on substrate 302. Power source 410 may include a battery, a capacitor bank, or another known power supply. Power source 410 may be electrically connected to one or more of the components of particle monitoring device 300 through bus 407, to power the connected components. For example, power source 410 may be electrically connected to one or more of micro sensors 308, clock 404, processor 406, or memory 408, to power the one or more of micro sensors 308, clock 404, processor 406, or memory 408.

Electronic circuitry 316 of particle monitoring device 300 may include additional components electrically connected to the components of particle monitoring device 300 described above. More particularly, electronic circuitry 316 may include a frequency source 412, e.g., a broad frequency source, or a detector 414. Frequency source 412 and/or detector 414 may be mounted on substrate 302. Frequency source 412 and detector 414 may have particular application in relation to specific embodiments of micro sensors 308 of particle monitoring device 300. Thus, further description of frequency source 412 and detector 414 is reserved for the corresponding sensor discussion below. Various embodiments of micro sensors 308 are now described.

Figures 5, 6:
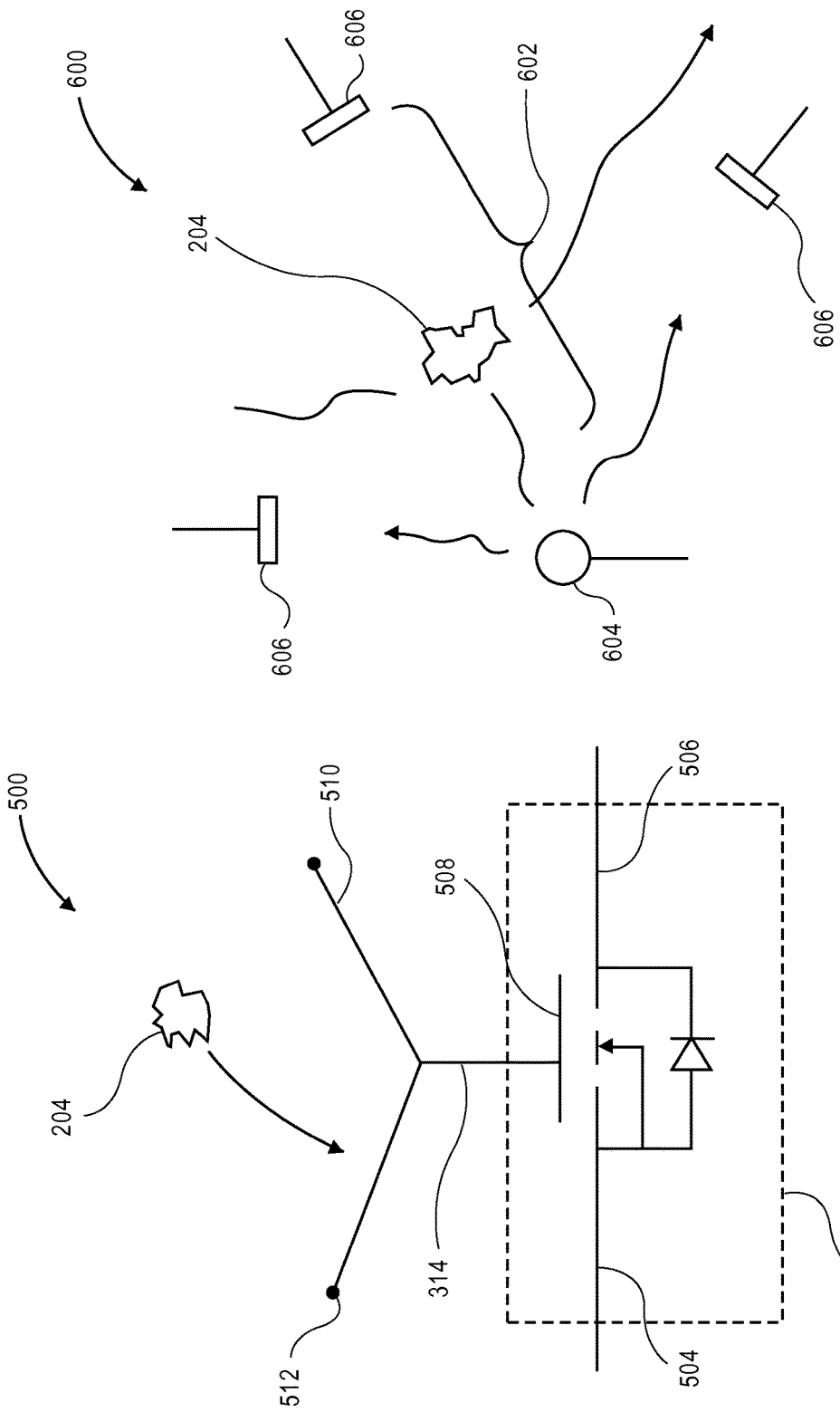
FIG. 5 is a schematic illustration of a transistor sensor type of micro sensor of a particle monitoring device, in accordance with an embodiment.
FIG. 6 is a schematic illustration of an optical sensor type of micro sensor of a particle monitoring device, in accordance with an embodiment.

Referring now to FIG. 5, a schematic illustration of a transistor sensor type of micro sensor of a particle monitoring device is illustrated in accordance with an embodiment. In an embodiment, one or more micro sensors 308 of particle monitoring device 300 include a transistor sensor 500. Transistor sensor 500 may include one or more transistor, e.g., a MOSFET 502. MOSFET 502 may include a source 504, a drain 506, and a gate 508. Transistor sensor 500 may also include a collector 510 to receive particle 204. In an embodiment, collector 510 is electrically connected to MOSFET 502. For example, collector 510 may be electrically connected to gate 508 of MOSFET 502 through electrical trace 314. Collector 510 may be physically separated from MOSFET 502, however, the subcomponents may be electrically connected with each other. Thus, MOSFET 502 may be configured to detect that a particle has landed on collector 510 even when collector 510 is located at a predetermined location spaced apart from MOSFET 502.

Collector 510 may be sized and configured to receive particle 204. For example, a typical size of particle 204 may be in a range of 45 nanometers to 1 micron, and thus, collector 510 may include an outer profile having an outer rim 512 with a diameter of at least 1 micron. A shape of outer rim 512 when viewed in a downward direction may be circular, rectangular, or any other shape. Furthermore, collector 510 may be flat, i.e., may have an essentially planar upper surface, or collector 510 may have a conical upper surface as shown in FIG. 5. In an embodiment, collector 510 is not a separate structure from MOSFET 502, but instead, is incorporated into MOSFET 502. For example, collector 510 may be a collection area on gate 508 of MOSFET 502. Gate 508 may be sized and patterned to receive particle 204.

In an embodiment, a parameter of transistor sensor 500 corresponds to MOSFET 502. More particularly, the parameter of transistor sensor 500 may be a threshold voltage of MOSFET 502 as measured across gate 508. The threshold voltage may correspond directly to the presence or absence of particle 204 on collector 510. For example, the threshold voltage may have a first value when particle 204 is not on collector 510, and the threshold voltage may have a second value (different than the first value) when particle 204 is on collector 510. Thus, particles 204 collected on a collector area of collector 510 may vary the threshold voltage of transistor sensor 500, i.e., the threshold voltage may change in response to particle 204 contacting collector 510. Processor 406 may be configured to detect a change in the threshold voltage, and thus, when a change in the threshold voltage is detected, particle monitoring device 300 can note the change as a particle contact and log the time and location of transistor sensor 500 that detected the event. It will be appreciated that, since transistor sensor 500 operates on the basis of electrical parameters that are independent of external pressures, particle monitoring device 300 having one or more micro sensors 308 such as transistor sensor 500 can work at any pressure regime, including under vacuum conditions.

Referring now to FIG. 6, a schematic illustration of an optical sensor type of micro sensor of a particle monitoring device is illustrated in accordance with an embodiment. In an embodiment, one or more micro sensors 308 of particle monitoring device 300 include an optical sensor 600. Optical sensor 600 may be a Micro-Opto-Electro-Mechanical Systems (MOEMS) as is known in the art, and may be formed directly on substrate 302 using known semiconductor processing operations. A description of the complexity and variety of MOEMS is not described here in favor of a simplified description for the purpose of brevity and ease of understanding. Optical sensor 600 may include a host of micro mirrors or lenses distributed across substrate 302. Without going into great detail, optical sensor 600 may include an optical path 602 emanating from a light source 604. Optical path 602 may be between light source 604 and a light detector 606. In an embodiment, a parameter of optical sensor 600 corresponds to whether light is received from light source 604 at light detector 606. For example, the parameter may change in response to particle 204 disturbing optical path 602. That is, when particle 204 passes through or rests in optical path 602 and blocks light between light source 604 and light detector 606, the parameter may change. In an embodiment, when particle 204 passes through optical sensor 600, light from light source 604 is reflected along a different optical path 602 toward another light detector 606. Detection of the reflected light by the other light detector 606 may result in a change to the parameter of optical sensor 600. The parameter may be, for example, an output voltage of optical sensor 600 corresponding to light detection. Processor 406 may be configured to detect a change in the output voltage, and thus, when a change in the output voltage and/or when a disturbance in optical path 602 is detected, particle monitoring device 300 can note the change as a particle contact and log the time and location of optical sensor 600 that detected the event.

Figure 7A:
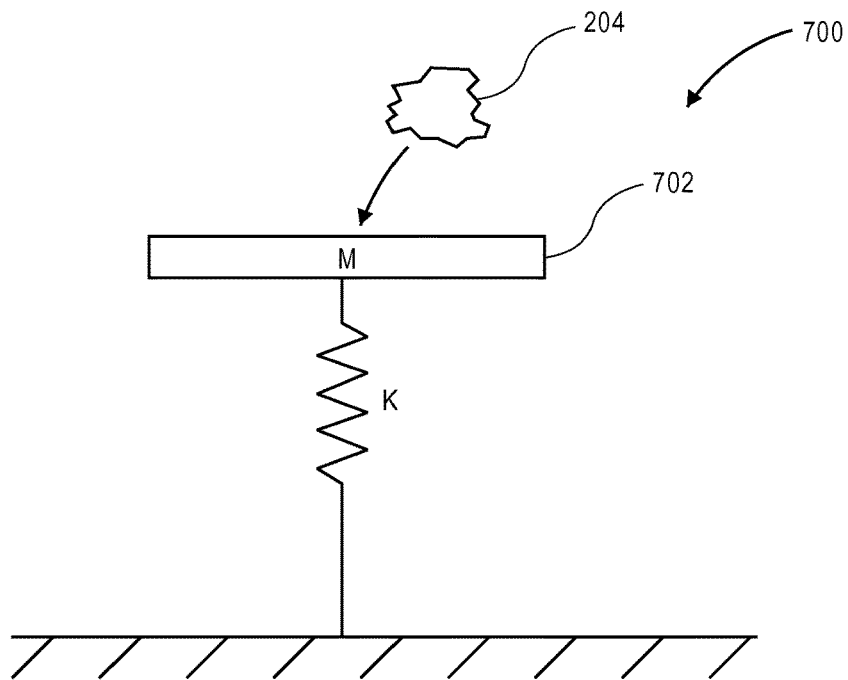
FIG. 7A-7B are schematic illustrations of micro-resonator types of micro sensors of a particle monitoring device, in accordance with an embodiment.

Referring now to FIG. 7A, a schematic illustration of a micro-resonator type of micro sensor of a particle monitoring device is illustrated in accordance with an embodiment. In an embodiment, one or more micro sensors 308 of particle monitoring device 300 include a micro-resonator 700. Micro-resonator 700 may be a suitable resonant mass sensor, such as a Quartz Crystal Microbalance (QCM), Surface Acoustic Wave (SAW), or Film Bulk Acoustic Resonators (FBAR), which are all known to quantify the cumulative mass of airborne particles deposited on their surfaces. A description of the complexity and variety of micro-resonators is not described here in favor of a simplified description for the purpose of brevity and ease of understanding. The micro-resonator(s) may be distributed at predetermined locations across support surface 304 of substrate 302. Each micro-resonator 700 may have a characteristic frequency, e.g., a resonant frequency, as is known in the art. For example, without going into great detail, micro-resonator 700 may be represented by a simple mass-spring system as is shown in FIG. 7A. The characteristic frequency of micro-resonator 700 may be inversely proportional to a mass 702 of the micro-resonator system. For example, the characteristic frequency may be proportional to sqrt(k/M) of the micro-resonator system, where 'M' corresponds to mass 702 and 'k' corresponds to a proportionality constant of the micro-resonator system. Thus, it will be recognized that the characteristic frequency shifts when micro-resonator 700 receives particle 204. More particularly, when particle 204 lands on micro-resonator 700 within processing chamber 108 of wafer processing tool 100, mass 702 of micro-resonator 700 changes, and accordingly, the characteristic frequency shifts.

Figure 7B:
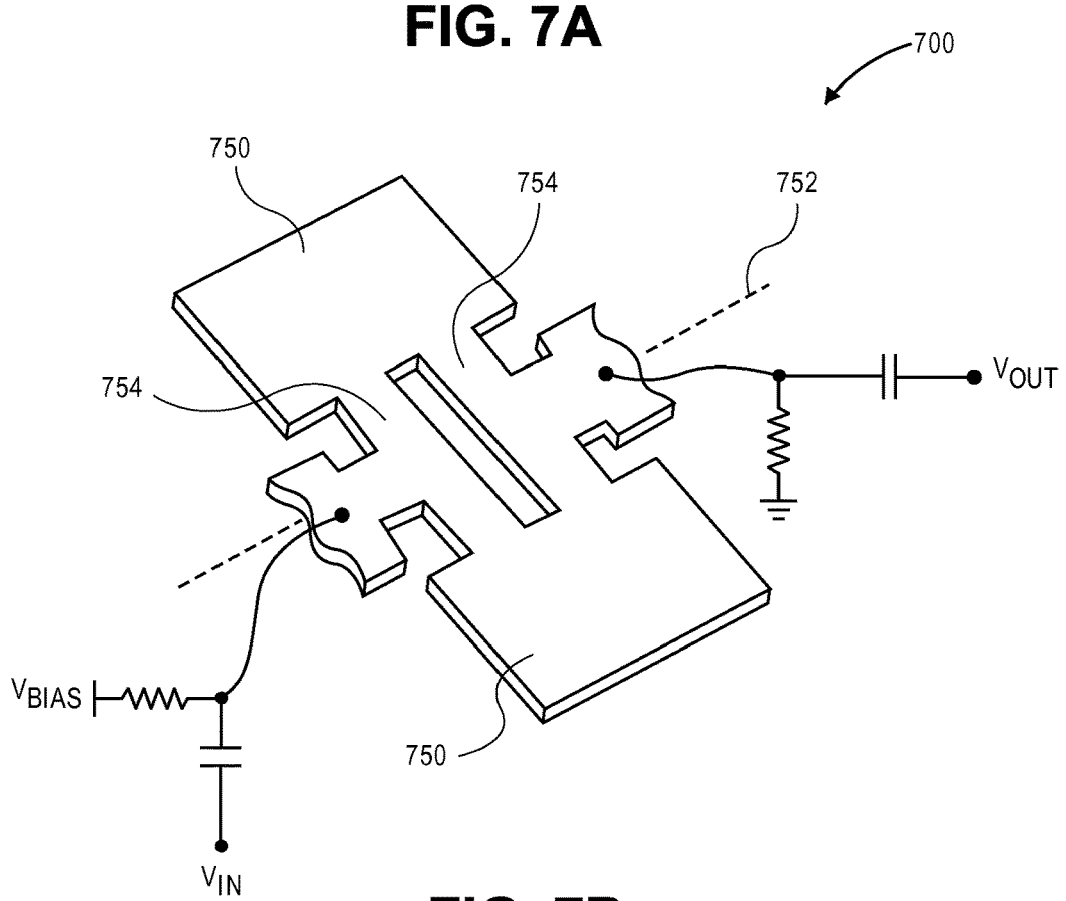

Referring now to FIG. 7B, a schematic illustration of a micro-resonator type of micro sensor of a particle monitoring device is illustrated in accordance with an embodiment. A particular type of micro-resonator 700 that may be used as a micro sensor 308 is a MEMS resonant mass sensor, such as a thermally actuated high-frequency single crystalline silicon resonator. Such micro-resonators 700 may be fabricated as individual devices or arrays using single mask processes. Micro-resonator may include two pads 750 on either side of a plane of symmetry 752. A fluctuating electrical current may be passed between the two pads 750 to cause an alternating current (AC) ohmic loss component in the current path. In an embodiment, most of the ohmic loss occurs in thin pillars 756 that interconnect the pads 750. Thin pillars 756 may be centrally located and extend between the pads 750 in a direction orthogonal to plane of symmetry 752. Fluctuating temperature generated in pillars 756 may cause an AC force, and an alternating thermal stress in pillars 756, to actuate micro-resonator 700 in an in-plane resonant mode. In the in-plane resonant mode, pads 750 having mass 'M' vibrate in opposite directions. Thus, at resonance, micro-resonator 700 includes a characteristic frequency of the vibrating pads 750, and a resistance of pillars 756 is modulated by an alternating mechanical stress due to a piezoresistive effect. Accordingly, there is a detectable small signal motional current in micro-resonator 700 corresponding to the characteristic frequency.

To detect a shift in the characteristic frequency of micro-resonator 700, frequency source 412 and detector 414 may be incorporated in electronic circuitry 316 of particle monitoring device 300. Frequency source 412 may be a broad frequency source that is used to excite micro-resonator 700. Detector 414 may monitor the characteristic frequency of micro-resonator 700, and detect a shift of the characteristic frequency. For example, detector 414 may output a signal corresponding to the characteristic frequency, e.g., an output voltage or current, to processor 406. Processor 406 may be configured to receive the output voltage and recognize the shift of the characteristic frequency. Thus, when a change in the output voltage and/or when the characteristic frequency of micro-resonator 700 changes, particle monitoring device 300 can note the change as a particle contact and log the time and location of micro-resonator 700 that detected the event. As mass 702 of micro-resonator 700 increases, e.g., as particles 204 accumulate on micro-resonator 700, the characteristic frequency will shift down, allowing particle monitoring device 300 to capture a history of particle 204 accumulation in addition to individual particle contact events.

Figure 8:
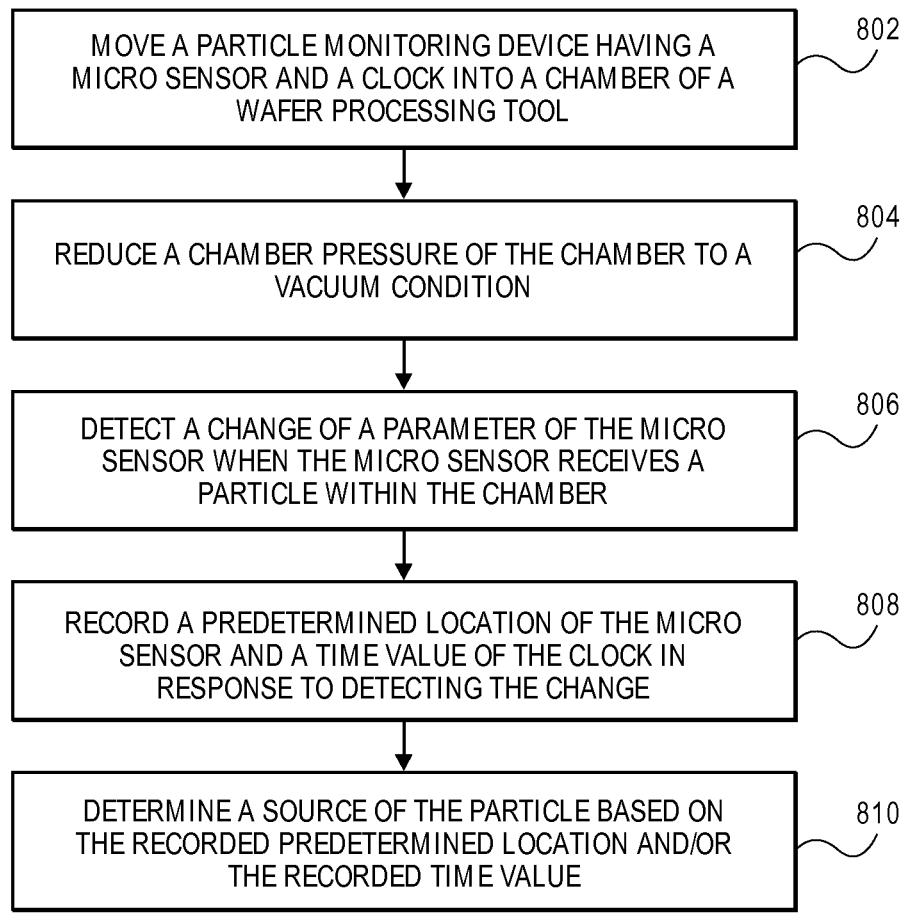
FIG. 8 is an illustration of a flowchart representing operations in a method for determining a source of a particle in a wafer processing tool, in accordance with an embodiment.

Referring now to FIG. 8, an illustration of a flowchart representing operations in a method for determining a source of a particle in a wafer processing tool is illustrated in accordance with an embodiment. At operation 802, particle monitoring device 300 is moved from a first chamber of wafer processing tool 100, e.g., buffer chamber 102, to a second chamber of wafer processing tool 100, e.g., processing chamber 108. Particle monitoring device 300 may have the structure and components described above, e.g., micro sensor 308 may be mounted at a predetermined location on support surface 304 and clock 404 may be mounted on substrate 302. Micro sensor 308 may have a parameter, and clock 404 may be configured to output a time value.

At operation 804, a chamber pressure of the second chamber, e.g., processing chamber 108, is reduced to a vacuum condition. More particularly, the chamber pressure may be lowered below 0.5 atm. As described above, particle monitoring device 300 is capable of detecting particles under all pressure regimes, and thus, may be used for real-time particle monitoring under the conditions normally seen by semiconductor wafer 202 in wafer processing tool 100.

At operation 806, a change of the parameter of micro sensor 308 is detected. More particularly, the change of the parameter may be detected when micro sensor 308 receives particle 204 within the second chamber, e.g., processing chamber 108. In an embodiment, detecting the change of the parameter includes detecting a change of a threshold voltage of MOSFET 502 in transistor sensor 500. In an embodiment, detecting the change of the parameter includes detecting a disturbance in optical path 602 of optical sensor 600. In an embodiment, detecting the change of the parameter includes detecting a shift of a characteristic frequency of micro-resonator 700. Thus, when micro sensor 308 detects a change in the parameter, a corresponding signal is provided.

At operation 808, the corresponding signal is used by processor 406 to record information about the particle event in response to detecting the change of the parameter. For example, processor 406 may record the predetermined location of micro sensor 308 on support surface 304. Accordingly, the precise location where particle 204 interacts with substrate 302 may be recorded. Processor 406 may record the time value output by clock 404. Accordingly, the precise time when particle 204 interacts with substrate 302 may be recorded.

At operation 810, the recorded information may be used to determine a source of particle 204. For example, the recorded predetermined location of micro sensor 308 that received particle 204 and/or the recorded time value corresponding to the particle event may be used to determine the component and/or the process operation performed by wafer processing tool 100 that led to the particle contamination.

In an embodiment, the recorded time value acts as a timestamp that can be synchronized with a log file of wafer processing tool 100. For example, wafer processing tool 100 may maintain a log file indicating a time at which every process operation begins and/or ends. Thus, by comparing the time value output by clock 404 (when particle 204 is detected by micro sensor 308) to the log file, a process operation concurrent with the particle event may be determined. By way of example, if the time value output indicates that the particle event occurred 5 minutes into the wafer manufacturing process, and the system log file indicates that a slit valve door of gate lock was opened at the 5 minute mark, it may be reasonably concluded that the slit valve door of gate lock, and/or the action of opening gate lock, is a source 504 contributing to particle contamination.

In a similar manner to the timestamp information, the information about the location of particle contact may be used to determine the particle source. For example, when several process operations occur simultaneously, e.g., lift pins rise when a slit valve door closes, a relative distance between the particle location and the active components may be used to infer which component is the source of the particle. That is, if the recorded location is nearer to the lift pins than to the slit valve door, it may be inferred that the lift pins are the source of the particle.

The information about particle contamination may be continuously logged during the wafer manufacturing process, and thus, the information may be made available for analysis in real-time or in near real-time. That is, particle monitoring device 300 may be connected wirelessly to other machines in a network using a wireless network interface device to monitor and analyze particle contamination data using a computer system remotely situated from particle monitoring device 300 in real-time. Alternatively, particle monitoring device 300 may be connected to the other machines via a data transfer cable as soon as particle monitoring device 300 completes the wafer manufacturing process of wafer processing tool 100 to analyze stored information in near real-time. Thus, a source of particle contamination may be quickly identified during or after the wafer manufacturing processes complete, and appropriate repairs may be made. Particle monitoring device 300 may be used as a process qualification operation prior to running batches of semiconductor wafers 202 through the wafer manufacturing process of wafer processing tool 100. Alternatively, particle monitoring device 300 may be used as a process troubleshooting tool to facilitate timely repairs of wafer processing tool 100 when particle contamination is identified within a batch of semiconductor wafers 202. Accordingly, particle monitoring device 300 provides a fast, inexpensive, and easy way to identify and eliminate a source of particle contamination in wafer processing tool 100.

Figure 9:
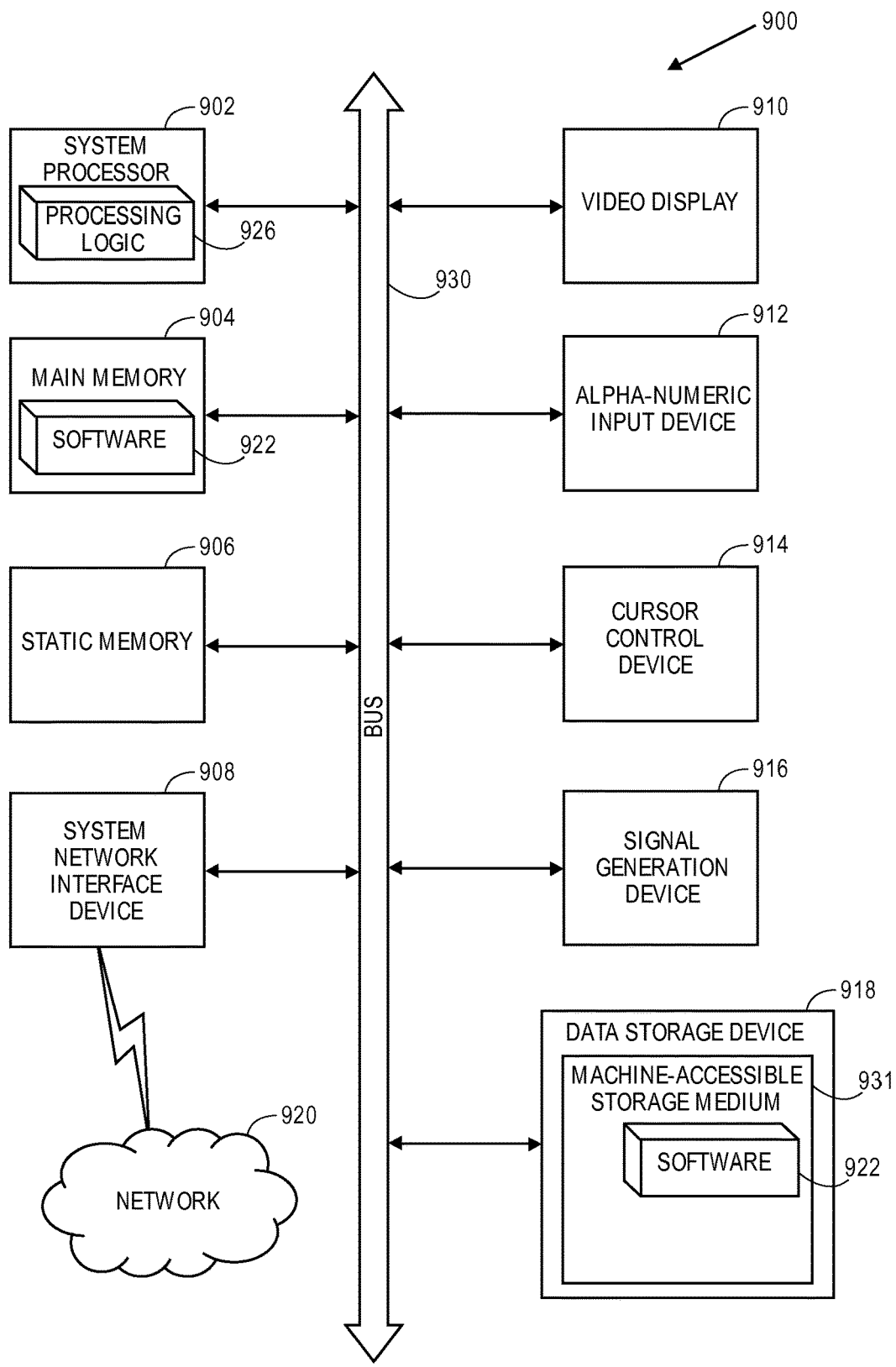
FIG. 9 illustrates a block diagram of an exemplary computer system of a wafer processing tool, in accordance with an embodiment.

Referring now to FIG. 9, a block diagram of an exemplary computer system of a wafer processing tool is illustrated in accordance with an embodiment. One or more components of the illustrated computer system 900 may be used in electronic circuitry 316 of particle monitoring device 300. Furthermore, wafer processing tool 100 may incorporate computer system 900. In an embodiment, computer system 900 is coupled to and controls robots, load locks, processing chambers, and other components of wafer processing tool 100. Computer system 900 may also provide a system log file for wafer processing tool 100 as discussed above. Computer system 900 may also receive and analyze particle event information provided by particle monitoring device 300. That is, the computer system 900 may be implemented in wafer processing tool 100 to control process operations of a wafer manufacturing process, generate a log file to record times and actions related to the process, and compare the log file data to data recorded by particle monitoring device 300 in order to determine a source 504 of particle contamination.

Computer system 900 may be connected (e.g., networked) to other machines in a Local Area Network (LAN), an intranet, an extranet, or the Internet. Computer system 900 may operate in the capacity of a server or a client machine in a client-server network environment, or as a peer machine in a peer-to-peer (or distributed) network environment. Computer system 900 may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated for computer system 900, the term "machine" shall also be taken to include any collection of machines (e.g., computers) that individually or jointly execute a set (or multiple sets) of instructions to perform any one or more of the methodologies described herein.

Computer system 900 may include a computer program product, or software 922, having a non-transitory machine-readable medium having stored thereon instructions, which may be used to program computer system 900 (or other electronic devices) to perform a process according to embodiments. A machine-readable medium includes any mechanism for storing or transmitting information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices, etc.), a machine (e.g., computer) readable transmission medium (electrical, optical, acoustical or other form of propagated signals (e.g., infrared signals, digital signals, etc.)), etc.

In an embodiment, computer system 900 includes a system processor 902, a main memory 904 (e.g., read-only memory (ROM), flash memory, dynamic random access memory (DRAM) such as synchronous DRAM (SDRAM) or Rambus DRAM (RDRAM), etc.), a static memory 906 (e.g., flash memory, static random access memory (SRAM), etc.), and a secondary memory 918 (e.g., a data storage device), which communicate with each other via a bus 930.

System processor 902 represents one or more general-purpose processing devices such as a microsystem processor, central processing unit, or the like. More particularly, the system processor may be a complex instruction set computing (CISC) microsystem processor, reduced instruction set computing (RISC) microsystem processor, very long instruction word (VLIW) microsystem processor, a system processor implementing other instruction sets, or system processors implementing a combination of instruction sets. System processor 902 may also be one or more special-purpose processing devices such as an application specific integrated circuit (ASIC), a field programmable gate array (FPGA), a digital signal system processor (DSP), network system processor, or the like. System processor 902 is configured to execute the processing logic for performing the operations described herein.

The computer system 900 may further include a system network interface device 908 for communicating with other devices or machines, e.g., particle monitoring device 300.

The computer system 900 may also include a video display unit 910 (e.g., a liquid crystal display (LCD), a light emitting diode display (LED), or a cathode ray tube (CRT)), an alphanumeric input device 912 (e.g., a keyboard), a cursor control device 914 (e.g., a mouse), and a signal generation device 916 (e.g., a speaker).

The secondary memory 918 may include a machine-accessible storage medium 931 (or more specifically a computer-readable storage medium) on which is stored one or more sets of instructions (e.g., software 922) embodying any one or more of the methodologies or functions described herein. The software 922 may also reside, completely or at least partially, within the main memory 904 and/or within the system processor 902 during execution thereof by the computer system 900, the main memory 904 and the system processor 902 also constituting machine-readable storage media. The software 922 may further be transmitted or received over a network 920 via the system network interface device 908.

While the machine-accessible storage medium 931 is shown in an exemplary embodiment to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies. The term "machine-readable storage medium" shall accordingly be taken to include, but not be limited to, solid-state memories, and optical and magnetic media.

In the foregoing specification, specific exemplary embodiments have been described. It will be evident that various modifications may be made thereto without departing from the scope of the following claims. The specification and drawings are, accordingly, to be regarded in an illustrative sense rather than a restrictive sense.

What is claimed is:

1. A particle monitoring device, comprising:
   a substrate having a support surface;
   a micro sensor mounted at a predetermined location on the support surface, wherein the micro sensor has a parameter, and wherein the parameter changes when the micro sensor receives a particle within a chamber of a wafer processing tool;
   a clock mounted on the substrate, wherein the clock is configured to output a time value;
   an accelerometer coupled directly to the clock, the accelerometer to trigger the clock to begin outputting a time value when the particle monitoring device enters or exits a chamber or a load lock of a wafer processing tool;
   a processor mounted on the substrate, wherein the processor is operably coupled to the micro sensor and the clock, and wherein the processor is configured to record the predetermined location and the time value when the parameter of the micro sensor changes.

2. The particle monitoring device of claim 1 further comprising a memory mounted on the substrate, wherein the processor is operably coupled to the memory to record the predetermined location and the time value in the memory.

3. The particle monitoring device of claim 2 further comprising a power source mounted on the substrate, wherein the power source is electrically coupled to one or more of the micro sensor, the clock, the processor, or the memory to power the one or more of the micro sensor, the clock, the processor, or the memory.

4. The particle monitoring device of claim 1, wherein the substrate includes a semiconductor material having a wafer form factor.

5. The particle monitoring device of claim 4, wherein the wafer form factor includes a diameter between 95 to 455 mm.

6. The particle monitoring device of claim 1, wherein the micro sensor includes:
- a MOSFET, wherein the parameter is a threshold voltage of the MOSFET, and
- a collector electrically coupled to the MOSFET, wherein the threshold voltage changes in response to the particle contacting the collector.

7. The particle monitoring device of claim 1, wherein the micro sensor includes an optical sensor having an optical path, and wherein the parameter changes in response to the particle disturbing the optical path.

8. A particle monitoring device, comprising:
- a substrate having a support surface;
- a micro-resonator mounted at a predetermined location on the support surface, wherein the micro-resonator has a characteristic frequency, and wherein the characteristic frequency shifts when the micro-resonator receives a particle within a chamber of a wafer processing tool;
- a clock mounted on the substrate, wherein the clock is configured to output a time value;
- a processor mounted on the substrate, wherein the processor is operably coupled to the micro-resonator and the clock, and wherein the processor is configured to record the predetermined location and the time value when the characteristic frequency of the micro-resonator shifts; and
- a broad frequency source mounted on the substrate to excite the micro-resonator.

9. The particle monitoring device of claim 8, wherein the characteristic frequency is inversely proportional to a mass of the micro-resonator, and wherein the mass of the micro-resonator changes when the micro-resonator receives the particle.

10. The particle monitoring device of claim 8 further comprising a detector mounted on the substrate to detect the shift of the characteristic frequency.

11. The particle monitoring device of claim 10 further comprising a memory mounted on the substrate, wherein the processor is operably coupled to the memory to record the predetermined location and the time value in the memory.

12. The particle monitoring device of claim 11 further comprising a power source mounted on the substrate, wherein the power source is electrically coupled to one or more of the micro-resonator, the clock, the processor, or the memory to power the one or more of the micro-resonator, the clock, the processor, or the memory.

13. The particle monitoring device of claim 8, wherein the substrate includes a semiconductor material having a wafer form factor.

14. The particle monitoring device of claim 13, wherein the wafer form factor includes a diameter between 95 to 455 mm.

* * * * *